(12) United States Patent
Ogihara et al.

(10) Patent No.: US 10,548,461 B2
(45) Date of Patent: Feb. 4, 2020

(54) ENDOSCOPE APPARATUS

(71) Applicant: OLYMPUS CORPORATION, Hachioji-shi, Tokyo (JP)

(72) Inventors: Tomoharu Ogihara, Higashimurayama (JP); Fumiyuki Okawa, Tama (JP); Keisuke Tsutsui, Kawaguchi (JP); Keisuke Ogawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/162,812

(22) Filed: May 24, 2016

(65) Prior Publication Data

US 2016/0262596 A1     Sep. 15, 2016

Related U.S. Application Data

(63) Continuation of application No. PCT/JP2015/065944, filed on Jun. 2, 2015.

(30) Foreign Application Priority Data

Sep. 3, 2014 (JP) ................................ 2014-179613

(51) Int. Cl.
*A61B 1/00*     (2006.01)
*A61B 1/04*     (2006.01)

(52) U.S. Cl.
CPC ...... *A61B 1/00055* (2013.01); *A61B 1/00006* (2013.01); *A61B 1/00027* (2013.01); *A61B 1/04* (2013.01); *A61B 1/0005* (2013.01)

(58) Field of Classification Search
CPC ............ A61B 1/00025; A61B 1/00027; A61B 1/00036; A61B 1/045; A61B 1/00193

USPC ................ 600/103, 111, 117, 118, 166, 143
See application file for complete search history.

(56) References Cited

U.S. PATENT DOCUMENTS 4,253,120 A * 2/1981 Levine ................. H04N 5/2176
                                                            348/246
5,305,098 A * 4/1994 Matsunaka ............... A61B 1/05
                                                             348/45
5,547,455 A * 8/1996 McKenna ............ A61B 1/0005
                                                             348/65

(Continued)

FOREIGN PATENT DOCUMENTS

CN     103006169 A     4/2013
JP     H09-84056 A     3/1997

(Continued)

OTHER PUBLICATIONS

Jul. 14, 2015 Search Report issued in International Patent Application No. PCT/JP2015/065944.

(Continued)

*Primary Examiner* — Timothy J Neal
*Assistant Examiner* — Jae Woo
(74) *Attorney, Agent, or Firm* — Oliff PLC

(57) ABSTRACT

An endoscope apparatus includes image sensors, a power supply unit, a failure detection unit, and a controller. The power supply unit supplies power independently to the image sensors. The failure detection unit detects a failure in each of the image sensors. The controller controls the power supply unit to stop power supply to an image sensor in which a failure is detected at the failure detection unit.

8 Claims, 2 Drawing Sheets

(56) References Cited

U.S. PATENT DOCUMENTS

| | | | | |
|---|---|---|---|---|
| 5,590,070 A * | 12/1996 | Harrand | ............ | G11C 11/4099 365/149 |
| 5,625,413 A * | 4/1997 | Katoh | ................ | H04N 5/3656 348/243 |
| 5,671,738 A * | 9/1997 | Thornberg | ............ | A61B 1/042 128/897 |
| 6,002,433 A * | 12/1999 | Watanabe | ............ | H04N 5/367 348/246 |
| 6,293,911 B1 * | 9/2001 | Imaizumi | ........... | A61B 1/00009 600/160 |
| 6,307,393 B1 * | 10/2001 | Shimura | ............ | H04N 5/23245 324/500 |
| 6,683,643 B1 * | 1/2004 | Takayama | ............ | H04N 5/367 348/247 |
| 6,954,225 B2 * | 10/2005 | Chen | ................ | G06T 7/254 348/152 |
| 7,512,250 B2 * | 3/2009 | Lim | ................ | G06K 9/00771 382/103 |
| 8,089,538 B2 * | 1/2012 | Kitani | ................ | H04N 5/23245 348/220.1 |
| 8,866,940 B2 * | 10/2014 | Tsutsui | ................ | H04N 5/367 348/241 |
| 2002/0014595 A1 | 2/2002 | Sendai et al. | | |
| 2003/0072483 A1 * | 4/2003 | Chen | ................ | G06T 7/596 382/154 |
| 2003/0169352 A1 * | 9/2003 | Kitani | ............ | H04N 5/367 348/247 |
| 2004/0080635 A1 * | 4/2004 | Hong | ............ | H04N 5/32 348/247 |
| 2004/0141640 A1 * | 7/2004 | Lee | ............ | G06T 7/0004 382/149 |
| 2004/0145664 A1 * | 7/2004 | Kobayashi | ............ | H04N 5/367 348/246 |
| 2004/0186351 A1 * | 9/2004 | Imaizumi | ............ | A61B 1/00009 600/160 |
| 2004/0193010 A1 * | 9/2004 | Fujimori | ............ | A61B 1/04 600/118 |
| 2005/0030395 A1 * | 2/2005 | Hattori | ............ | H04N 5/3675 348/246 |
| 2005/0033117 A1 * | 2/2005 | Ozaki | ............ | A61B 1/00009 600/109 |
| 2005/0231617 A1 * | 10/2005 | Kitani | ............ | H04N 9/646 348/246 |
| 2006/0007331 A1 * | 1/2006 | Izumi | ............ | H04N 5/367 348/246 |
| 2006/0252988 A1 * | 11/2006 | Ayame | ............ | A61B 1/00009 600/109 |
| 2007/0002134 A1 * | 1/2007 | Ishihara | ............ | G02B 23/2476 348/65 |
| 2007/0035643 A1 * | 2/2007 | Hashimoto | ......... | H04N 5/3675 348/246 |
| 2007/0146508 A1 * | 6/2007 | Oshima | ............ | H04N 5/361 348/243 |
| 2008/0005767 A1 * | 1/2008 | Seo | ............ | H04N 7/163 725/62 |
| 2008/0027284 A1 | 1/2008 | Suda | | |
| 2008/0045789 A1 * | 2/2008 | Sawachi | ............ | A61B 1/00183 600/111 |
| 2008/0218610 A1 * | 9/2008 | Chapman | ............ | H04N 17/002 348/246 |
| 2009/0062613 A1 * | 3/2009 | Mitsuhashi | ........ | A61B 1/00009 600/118 |
| 2009/0066793 A1 | 3/2009 | Takeda | | |
| 2009/0093807 A1 * | 4/2009 | Hyde | ............ | A61B 5/0071 606/34 |
| 2009/0118578 A1 * | 5/2009 | Takasugi | ............ | A61B 1/043 600/109 |
| 2009/0209818 A1 * | 8/2009 | Higuchi | ............ | A61B 1/00059 600/118 |
| 2009/0244273 A1 * | 10/2009 | Usami | ............ | G01R 31/318519 348/76 |
| 2010/0066872 A1 * | 3/2010 | Yamaguchi | ............ | H04N 5/367 348/246 |
| 2011/0032393 A1 * | 2/2011 | Yamaguchi | ............ | H04N 5/367 348/247 |
| 2011/0222098 A1 * | 9/2011 | Fukuda | ................ | G06F 3/1213 358/1.13 |
| 2011/0242300 A1 * | 10/2011 | Hashimoto | ........ | H04N 5/23203 348/65 |
| 2012/0033050 A1 * | 2/2012 | Komuro | ............ | H04N 13/0025 348/49 |
| 2012/0050550 A1 * | 3/2012 | Oba | ................... | H04N 5/23203 348/207.99 |
| 2012/0050586 A1 * | 3/2012 | Kanemitsu | ............ | H04N 5/3675 348/246 |
| 2012/0069157 A1 * | 3/2012 | Nonaka | ............ | H04N 5/23293 348/51 |
| 2012/0092473 A1 * | 4/2012 | Takamatsu | ......... | A61B 1/00009 348/74 |
| 2012/0113301 A1 * | 5/2012 | Ueda | ............ | H04N 5/367 348/246 |
| 2012/0127294 A1 * | 5/2012 | Yamaguchi | ............ | H04N 5/361 348/73 |
| 2013/0030248 A1 * | 1/2013 | Matsumaru | ........ | A61B 1/00027 600/110 |
| 2013/0169775 A1 * | 7/2013 | Ono | ............ | A61B 1/00009 348/68 |
| 2013/0242139 A1 * | 9/2013 | Kitani | ................ | H04N 5/2355 348/239 |
| 2013/0265403 A1 * | 10/2013 | Okawa | ............ | A61B 1/04 348/76 |
| 2014/0211049 A1 * | 7/2014 | Tsutsui | ............ | H04N 5/372 348/246 |
| 2015/0049206 A1 * | 2/2015 | Eshita | ............ | H04N 5/2251 348/207.11 |
| 2016/0128553 A1 * | 5/2016 | Geng | ............ | A61B 5/0064 600/111 |
| 2017/0046842 A1 * | 2/2017 | Yamaguchi | ........ | A61B 1/00009 |
| 2017/0230634 A1 * | 8/2017 | Takenouchi | ......... | H04N 13/204 |

FOREIGN PATENT DOCUMENTS

| | | |
|---|---|---|
| JP | 2002-045330 A | 2/2002 |
| JP | 2004-040480 A | 2/2004 |
| JP | 2008-012109 A | 1/2008 |
| JP | 2008-093029 A | 4/2008 |
| JP | 2011-206335 A | 10/2011 |
| JP | 2013-070322 A | 4/2013 |
| JP | 2013-090969 A | 5/2013 |
| WO | 2006/120815 A1 | 11/2006 |

OTHER PUBLICATIONS

Nov. 10, 2015 Office Action issued in Japanese Patent Application No. 2015-546742.

Mar. 7, 2017 International Preliminary Report on Patentability issued in International Application No. PCT/JP2015/065944.

Apr. 17, 2018 extended European Search Report issued in European Application No. 15837233.4.

Nov. 6, 2017 Office Action issued in Chinese Application No. 201580003861.8.

* cited by examiner

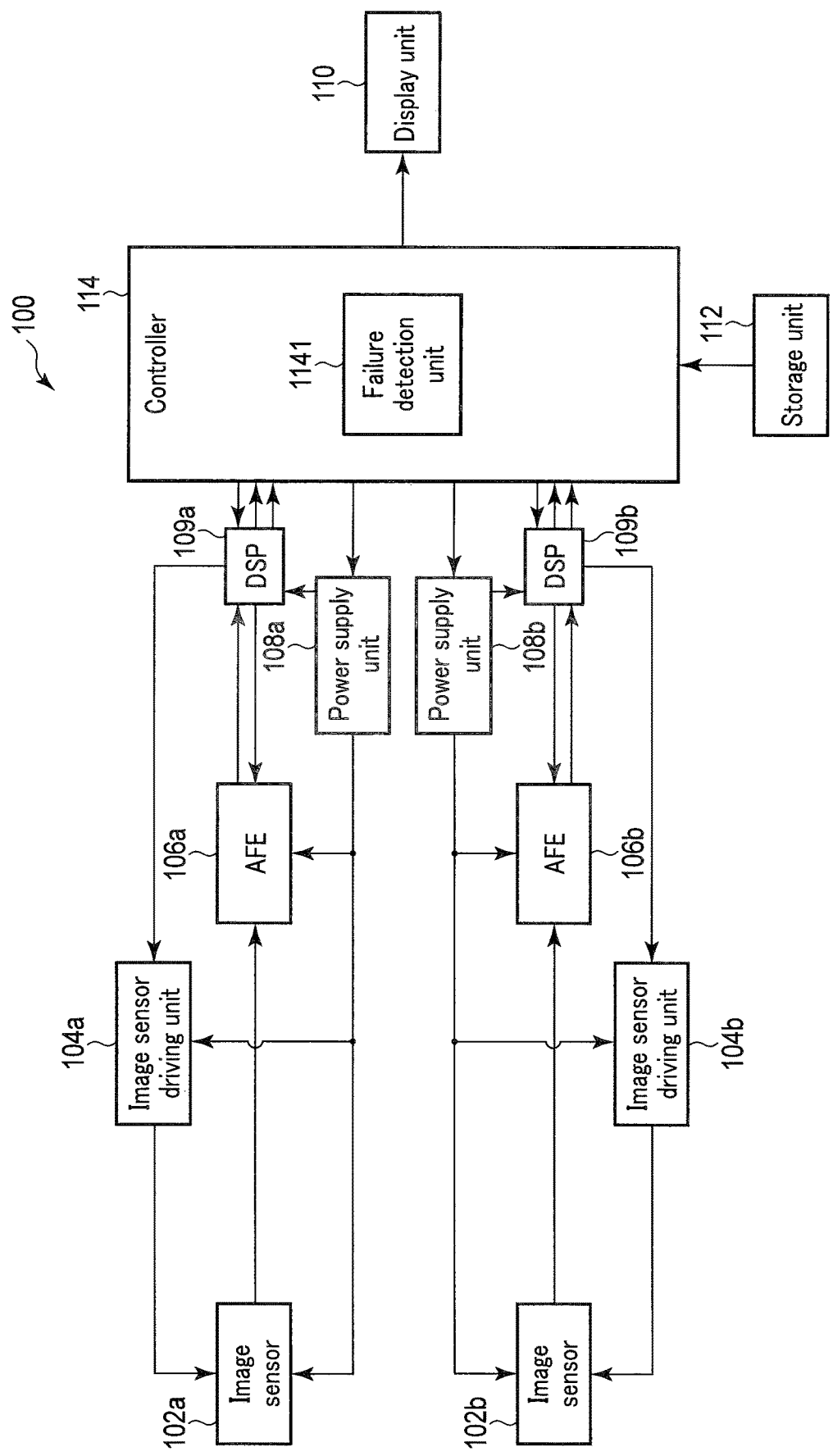
F I G. 1

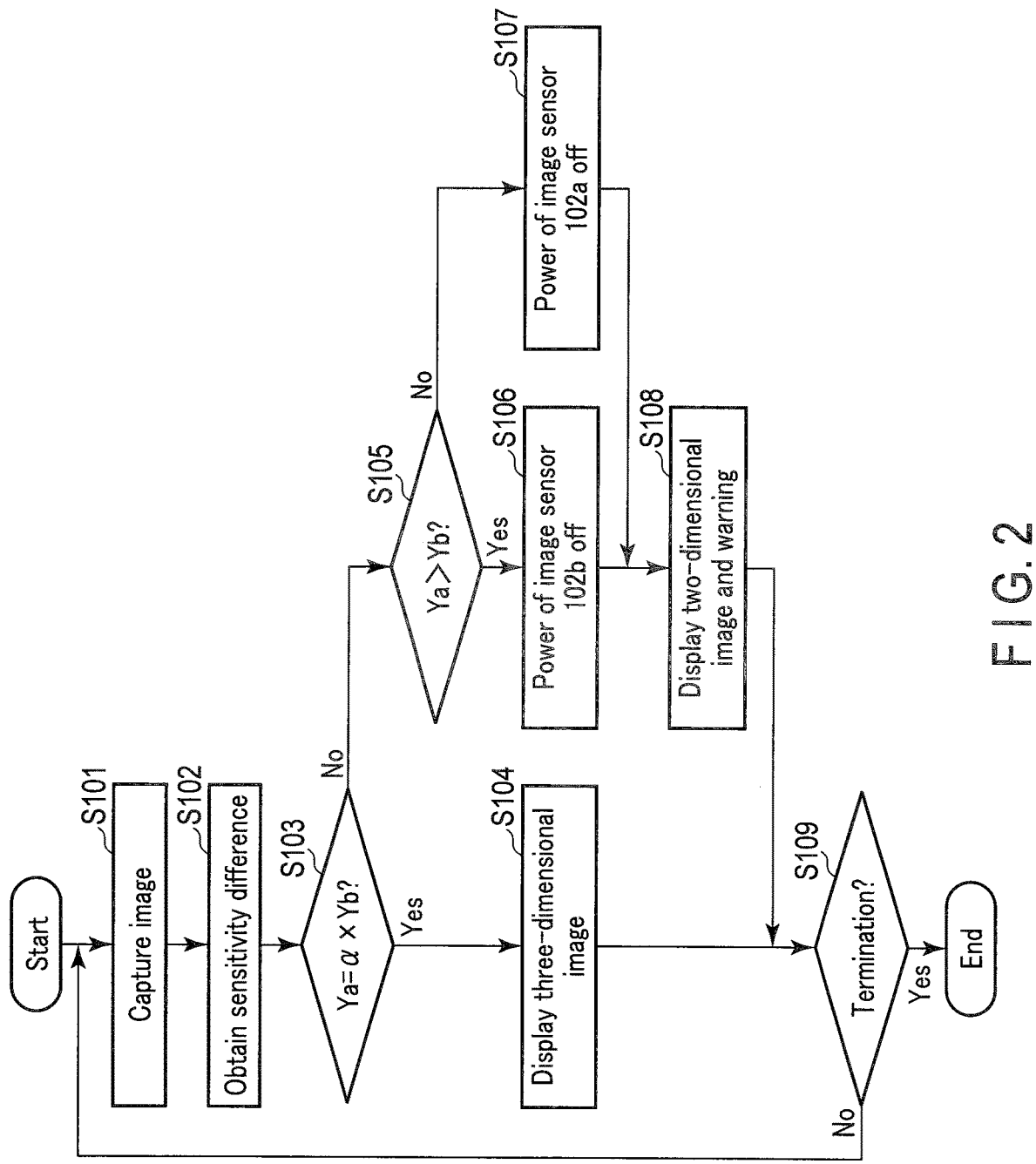
F I G. 2

ENDOSCOPE APPARATUS

CROSS-REFERENCE TO RELATED APPLICATIONS

This application is a Continuation Application of PCT Application No. PCT/JP2015/065944, filed Jun. 2, 2015 and based upon and claiming the benefit of priority from the prior Japanese Patent Application No. 2014-179613, filed Sep. 3, 2014, the entire contents of both of which are incorporated herein by reference.

BACKGROUND OF THE INVENTION

1. Field of Invention

The present invention relates to an endoscope apparatus.

2. Description of Related Art

Endoscope apparatuses that capture an image of a subject as a target object by a plurality of image sensors are known. The endoscope apparatuses include, for example, three-dimensional endoscope apparatuses. The three-dimensional endoscope apparatuses are configured to capture an image of a subject by a plurality of image sensors having parallax. A stereoscopic image is generated by performing suitable image processing to image signals obtained by the plurality of image sensors having parallax.

Various factors may cause a failure in the image sensors. Such a failure of the image sensors can be detected, for example, by the known technique as described in Jpn. Pat. Appln. KOKAI Publication No. 2002-45330. The apparatus of Jpn. Pat. Appln. KOKAI Publication No. 2002-45330 detects a failure in high sensitivity image sensor for an autofluorescence image and an image sensor for a normal image, and displays an image by switching from the image sensor where a failure is detected to the image sensor with no failure.

BRIEF SUMMARY OF THE INVENTION

An endoscope apparatus according to an aspect of the invention comprises: a plurality of image sensors that capture an image of a subject; a power supply unit that supplies power independently to the plurality of image sensors; a failure detection unit that detects a failure in each of the plurality of image sensors; and a controller that controls the power supply unit to stop power supply to an image sensor in which a failure is detected at the failure detection unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a block diagram showing an exemplary configuration of an endoscope apparatus according to an embodiment; and FIG. 2 is a flowchart showing the operation of the endoscope apparatus according to an embodiment.

DETAILED DESCRIPTION OF THE INVENTION

Hereinafter, embodiments of the present invention will be described with reference to the drawings.

FIG. 1 is a block diagram showing an exemplary configuration of an endoscope apparatus according to an embodiment. FIG. 1 merely shows the main structure of the endoscope apparatus according to the embodiment. As shown in FIG. 1, an endoscope apparatus 100 includes image sensors 102a and 102b, image sensor driving units 104a and 104b, analog front end (AFE) circuits 106a and 106b, power supply units 108a and 108b, digital signal processing (DSP) circuits 109a and 109b, a display unit 110, a storage unit 112, and a controller 114.

The image sensors 102a and 102b have pixels arranged in a two-dimensional matrix, capture an image of a subject through a lens not shown in the drawings, and generate an image signal of the subject. For the case where the endoscope apparatus 100 is a three-dimensional endoscope, the image sensors 102a and 102b have the same configuration, and are arranged to have a predetermined parallax. For example, the image sensor 102a generates an image signal for the right eye, and the image sensor 102b generates an image signal for the left eye.

The image sensor driving unit 104a controls the timing for capturing an image by the image sensor 102a and the timing for reading the image signal generated at the image sensor 102a, in accordance with control by the controller 114. The image sensor driving unit 104b controls the timing for capturing an image by the image sensor 102b and the timing for reading the image signal generated at the image sensor 102b, in accordance with control by the controller 114.

The AFE 106a performs various analog processing, such as gain adjustment, relative to the image signal read from the image sensor 102a. The AFE 106a also converts the image signal subjected to analog processing into image data which is a digital signal. The image data obtained at the AFE 106a is output to the DSP 109a as parallel data. The AFE 106b performs various analog processing, such as gain adjustment, relative to the image signal read from the image sensor 102b. The AFE 106b also converts the image signal subjected to analog processing into image data which is a digital signal. The image data obtained at the AFE 106b is output to the DSP 109b as parallel data.

The DSP 109a performs setting of a driving pattern (such as the exposure time of image sensor 102a, the gain amount of image signal at the AFE 106a, etc.) for driving the image sensor 102a to the image sensor driving unit 104a and the AFE 106a, in accordance with the type of the image sensor 102a. In addition, the DSP 109a converts the image data input as parallel data from the AFE 106a to serial data such as LVDS data, and outputs the converted data to the controller 114. The DSP 109b performs setting of the driving pattern (such as the exposure time of image sensor 102b, the gain amount of image signal at the AFE 106b, etc.) for driving the image sensor 102a to the image sensor driving unit 104b and the AFE 106b, in accordance with the type of the image sensor 102b. In addition, the DSP 109b converts the image data input as parallel data from the AFE 106b into serial data such as LVDS data, and outputs the converted data to the controller 114.

The display unit 110 displays an image based on the image data obtained at the DSP 109a and the DSP 109b and image-processed at the controller 114. For the case where the endoscope apparatus 100 is a three-dimensional endoscope, the display unit 110 is configured to switch and display a two-dimensional image and a three-dimensional image. Various methods such as a liquid crystal GRIN lens method are applied to the display unit that is capable of displaying two-dimensional and three-dimensional images.

The storage unit 112 stores a control program of the endoscope apparatus 100 that is executed by the controller 114. The storage unit 112 also stores sensitivity differences for each pixel of the image sensor 102a and the image sensor 102b. The sensitivity difference is the ratio of difference between the output signals of the image sensors 102a and 102b that is caused due to a design error of the image sensors 102a and 102b. The sensitivity differences are measured at the time of manufacturing the endoscope apparatus 100, for example, and stored at the storage unit 112.

The controller 114 controls the operation of the endoscope apparatus 100. For example, the controller 114 controls the operation of the image sensor driving unit 104a and the image sensor driving unit 104b by inputting a control signal to the image sensor driving unit 104a and the image sensor driving unit 104b through the DSP 109a or the DSP 109b. The control signal is, for example, a signal to instruct the driving pattern of the image sensors 102a and 102b. In addition, the controller 114 processes image data from the DSP 109a and the DSP 109b, and generates a two-dimensional image or a three-dimensional image. The controller 114 also corrects image data in accordance with the sensitivity difference when generating a three-dimensional image. For example, the case where the image data obtained through the image sensor 102b is corrected will be explained. It is assumed that a pixel value of a certain pixel within the image data obtained through the image sensor 102b before correction is Yb, a corrected pixel value is Yb', a sensitivity difference is α, and the correction for each pixel performed by the controller 114 is given as the following equation 1:

$$Yb' = \alpha \times Yb \qquad \text{(Equation 1)}$$

The controller 114 has a failure detection unit 1141. The failure detection unit 1141 detects a failure in the image sensors 102a and 102b based on the image data (image data A) obtained through the image sensor 102a and the image data (image data B) obtained through the image sensor 102b. The controller 114 controls the power supply unit 108a and the power supply unit 108b in accordance with the detection results of the failure detection unit 1141 to turn on and off the power supply for the image sensors 102a and 102b, the image sensor driving units 104a and 104b, the AFEs 106a and 106b, and the DSPs 109a and 109b.

Next, the operation of the endoscope apparatus 100 according to the embodiment will be explained. FIG. 2 is a flowchart showing the operation of the endoscope apparatus 100. The operation shown in FIG. 2 is controlled by the controller 114.

For example, the operation shown in FIG. 2 is initiated as the power supply of the endoscope apparatus 100 is turned on. In step S101, the controller 114 initiates image capture by the image sensors 102a and 102b to display an endoscope image on the display unit 110. That is, the controller 114 controls the power supply unit 108a to supply driving power to each of the image sensor 102a, the image sensor driving unit 104a, the AFE 106a, and the DSP 109a, and controls the power supply unit 108b to supply driving power to each of the image sensor 102b, the image sensor driving unit 104b, the AFE 106b, and the DSP 109b. Then, the controller 114 controls the image sensor driving unit 104a through the DSP 109a to initiate image capture by the image sensor 102a, and controls the image sensor driving unit 104b through the DSP 109b to initiate image capture by the image sensor 102b.

In step S102, the failure detection unit 1141 of the controller 114 obtains a sensitivity difference from the storage unit 112.

In step S103, the failure detection unit 1141 determines whether equation 2 is true by comparing the corresponding pixels in the image data A and the image data B. In equation 2, "Ya" is a pixel value of a reference pixel (may be one or more) within the image data A, "Yb" is a pixel value of a pixel within the image data B corresponding to the reference pixel, "α" is a sensitivity difference, and "Ynoise" is a noise component.

$$Ya = \alpha \times Yb + Ynoise \qquad \text{(Equation 2)}$$

In the case where the same image of the subject is formed at the image sensors 102a and 102b, as a three-dimensional endoscope apparatus, the pixel values of the corresponding pixels in the image data A and the image data B usually become equal in consideration of the sensitivity difference α and the noise component Ynoise. In contrast, if a failure such as a short-circuit occurs in either of the image sensors 102a and 102b, the pixel values of the corresponding pixels in the image data A and the image data B do not become equal even in consideration of the sensitivity difference α. By determining whether equation 2 is true or not, it is possible to determine whether a failure occurs in the image sensor system. When the determination of step S103 is performed to a plurality of pixels, it is determined that equation 2 is true if equation 2 is true for a predetermined number of pixels or more, for example. In addition, a similar determination to equation 2 may be performed by applying the sum of the pixel values before and after correction to "Ya" and "Yb".

When it is determined that equation 2 is true in step S103, the processing proceeds to step S104. In step S104, the controller 114 processes the image data A and the image data B, and generates a three-dimensional image of the subject. The generation of the three-dimensional image is performed by using the known method. After generation of the three-dimensional image, the controller 114 controls the display unit 110 to display the three-dimensional image.

When it is determined that equation 2 is not true in step S103, the processing proceeds to step S105. In step S105, the failure detection unit 1141 determines whether Ya is greater than Yb. This comparison may be performed to a pair of pixels, or a plurality of pairs of pixels.

When it is determined that Ya is greater than Yb in step S105, the processing proceeds to step S106. In the embodiment, if Ya is greater than Yb, it is assumed that a correct image signal is not input from the image sensor 102b to the controller 114 due to a failure in the image sensor 102b system. In this case, the controller 114 turns off the power supply of the image sensor 102b in step S106. That is, the controller 114 controls the power supply unit 108b to stop supplying power to the image sensor 102b, the image sensor driving unit 104b, the AFE 106b, and the DSP 109b.

When it is determined that Ya is not greater than Yb in step S105, i.e., determined that Yb is greater than Ya, the processing proceeds to step S107. In the embodiment, if Yb is greater than Ya, it is assumed that a correct image signal is not input from the image sensor 102a to the controller 114 due to a failure in the image sensor 102a system. In this case, the controller 114 turns off the power supply of the image sensor 102a in step S107. That is, the controller 114 controls the power supply unit 108a to stop supplying power to the image sensor 102a, the image sensor driving unit 104a, the AFE 106a, and the DSP 109a.

In step S108, the controller 114 generates a two-dimensional image of the subject based on the image data obtained through the image sensor for which the power supply is not turned off. After generation of the two-dimensional image, the controller 114 controls the display unit 110 to display the two-dimensional image. Furthermore, the controller 114 controls the display unit 110 to display, for example, a message to warn that a failure occurs in the image sensor. Upon reception of a warning, the operator removes the endoscope apparatus 100 from the subject. In this embodiment, the warning is displayed on the display unit 110, but may be displayed on a display unit other than the display unit 110. Otherwise, the warning may be given by another method, such as a voice message.

In step S109, the controller 114 determines whether or not to terminate the operation of the endoscope apparatus 100. For example, if the power supply switch not shown in the drawings is turned off, it is determined that the operation of the endoscope apparatus 100 is terminated. When it is determined that the operation of the endoscope apparatus 100 is not terminated in step S109, the processing is returned to step S101. When it is determined that the operation of the endoscope apparatus 100 is terminated in step S109, the operation shown in FIG. 2 is terminated.

According to the embodiment as explained above, in the case where it is difficult to continuously use the endoscope apparatus having a plurality of image sensors due to a failure in an image sensor, only the power supply of the image sensor in which a failure is detected is turned off. By this operation, it is possible to display a two-dimensional endoscope image by using a normal image sensor. Therefore, the operator can remove the endoscope apparatus 100 while looking at the images necessary for the remove.

In addition, in the case where it is difficult to continuously use the endoscope apparatus, the warning is given to the operator in addition to displaying the endoscope image. By the warning, the operator immediately notices a failure in the image sensor.

The variation example of the embodiment will be explained below. In the aforementioned embodiment, a failure in an image sensor is detected by comparing the pixel values of a pixel of image data A and the corresponding pixel of image data B in consideration of the sensitivity difference. However, a method for detecting a failure in an image sensor is not limited thereto.

For example, if there is an image sensor that cannot obtain a predetermined amount of exposure light even after a predetermined time has elapsed, it can be assumed that a failure occurs in the image sensor.

In addition, an image sensor usually has a defective pixel. One of known methods for correcting the pixel value of the defective pixel is assuming as a defective pixel a pixel having a pixel value equal to or greater than a threshold while the image sensor is driven, and correcting the pixel value of the defective pixel by using the pixel values of neighboring pixels of the defective pixel, in addition to pre-storing a position of a defective pixel. With this method, a failure in the image sensor can be detected. For example, it is assumed that the number of defective pixels of the image sensor 102a is a, and the number of defective pixels of the image sensor 102b is b. If a malfunction occurs in the system of the image sensor 102b, and the temperature of the image sensor 102b becomes high, the number of pixels deemed to be defective pixels becomes greater than b. On the other hand, if the image sensor 102b is short-circuited, the image sensor 102b is not driven, and the number of pixels deemed to be defective pixels becomes less than b (near zero). Accordingly, a failure in the system of the image sensor can be detected based on the change in the number of defective pixels.

In addition, a failure in the system of the image sensor can also be detected by the sequential change in the sum of the pixel values of a plurality of pixels. For example, it is assumed that a current determination time is t, an added value of pixel values of image data A at the time t is At, and an added value of pixel values of image data B at the time t is Bt. In addition, it is assumed that a determination time immediately prior to the current determination time is t−1, an added value of pixel values of image data A at the time t−1 is At−1, and an added value of pixel values of image data B at the time t−1 is Bt−1. It is considered that the change in image of the subject for a short time is small. Thus, the difference between the added values between the time t−1 and the time t is usually small. On the other hand, the difference between the added values between the time t−1 and the time t becomes large if a malfunction occurs in the system of the image sensor. That is, it is determined that a malfunction occurs in the image sensor when equation 3 or 4 is true. In equations 3 and 4, "abs" indicates obtaining an absolute value, and "β" indicates a threshold.

(Case where a malfunction occurs in image sensor 102a system)

$$\mathrm{abs}\{(At)-(At-1)\} > \beta \qquad \text{Equation 3}$$

(Case where a malfunction occurs in image sensor 102b system)

$$\mathrm{abs}\{(Bt)-(Bt-1)\} > \beta \qquad \text{Equation 4}$$

This determination can be applied to determining a deterioration of image data due to contamination of a lens or an image sensor, in addition to determining a malfunction. Accordingly, the determination can be applied to avoid using depleted image data, for example.

In addition, a method for constantly or intermittently measuring the temperature or current (value of image signal) of each image sensor may be applied. In this case, if an image sensor exhibits the temperature exceeding a certain value, or outputs an image signal having a value greater than a certain value, the image sensor is determined as having a failure. In the aforementioned embodiment, the power supply units each corresponding to the two image sensors are provided. However, if power can be supplied to the two image sensors independently, the number of power supply units is not limited to two. In the aforementioned embodiment, a three-dimensional endoscope apparatus is adopted as the endoscope apparatus 100. However, the technique of the embodiment can be applied not only to the three-dimensional endoscope apparatus, but also to any kind of endoscope apparatus having a plurality of image sensors. The number of image sensors is not limited to two. The technique of the embodiment can be applied to an endoscope apparatus having a three-plate image sensor, for example.

What is claimed is:
1. An endoscope apparatus comprising:
   an endoscope body configured to be inserted into and removed from an identical opening in a subject;
   a plurality of image sensors that are configured to capture an image of a subject;

a plurality of power supplies that are configured to supply power independently to the plurality of image sensors; and a controller that is configured to:
   detect whether a failure has occurred in each of the plurality of image sensors; and
   control the plurality of power supplies to stop power supply to an image sensor in which a failure is detected, while simultaneously continuing power supply to an image sensor in which a failure is not detected to generate the image of the subject for securing a field of view for removal of the endoscope body.

2. The endoscope apparatus according to claim 1, wherein the controller is configured to output a warning indicating that a failure is detected when the failure is detected.

3. The endoscope apparatus according to claim 1, wherein the controller is configured to detect a failure in each of the plurality of image sensors based on a difference between pixel values of corresponding pixels between a plurality of pieces of image data obtained from the plurality of image sensors, and on a sensitivity difference between the plurality of image sensors.

4. The endoscope apparatus according to claim 1, wherein the controller is configured to detect a failure in each of the plurality of image sensors based on a change in a number of defective pixels in the plurality of image sensors.

5. The endoscope apparatus according to claim 1, wherein the controller is configured to detect a failure in each of the plurality of image sensors based on a change over time in a sum of pixel values of a plurality of pixels in each of a plurality of pieces of image data obtained from the plurality of image sensors.

6. The endoscope apparatus according to claim 1, further comprising:
   a display that is configured to display an image based on a plurality of pieces of image data obtained from the plurality of image sensors, wherein the controller is configured to control the display to display an image based on image data obtained from an image sensor in which a failure is not detected when the failure is detected.

7. The endoscope apparatus according to claim 1, wherein the plurality of image sensors comprises:
   a first image sensor, and
   a second image sensor configured to capture a region including an identical field of view as the first image sensor.

8. The endoscope apparatus according to claim 1, wherein:
   the plurality of image sensors comprises a first image sensor configured to capture a first image of the subject, and a second image sensor configured to capture a second image of the subject,
   the second image sensor is arranged at a position having parallax with respect to the first image sensor, and
   the controller is configured to:
      generate a three-dimensional image based on the first image and the second image when the failure is not detected in the first image sensor or the second image sensor, and
      generate a two dimensional image based on an image obtained by one of the first image sensor and the second image sensor when the failure is detected in the other of the first image sensor and the second image sensor.

* * * * *